(12) United States Patent
Ure

(10) Patent No.: US 9,149,736 B2
(45) Date of Patent: Oct. 6, 2015

(54) DEHYDRATION OF ACETIC ACID BY AZEOTROPIC DISTILLATION IN THE PRODUCTION OF AN AROMATIC ACID

(71) Applicant: INVISTA North America S.a.r.l., Wilmington, DE (US)

(72) Inventor: Alan Macpherson Ure, Cleveland (GB)

(73) Assignee: INVISTA North America S.a.r.l., Wilmington, DE (US)

( * ) Notice: Subject to any disclaimer, the term of this patent is extended or adjusted under 35 U.S.C. 154(b) by 231 days.

(21) Appl. No.: 13/826,106

(22) Filed: Mar. 14, 2013

(65) Prior Publication Data

US 2014/0166469 A1 Jun. 19, 2014

Related U.S. Application Data

(60) Provisional application No. 61/736,897, filed on Dec. 13, 2012.

(51) Int. Cl.
*B01D 3/36* (2006.01)
*C07C 51/46* (2006.01)
*C07C 7/00* (2006.01)
*B01D 3/42* (2006.01)

(52) U.S. Cl.
CPC . *B01D 3/36* (2013.01); *C07C 7/005* (2013.01); *C07C 51/46* (2013.01); *B01D 3/42* (2013.01)

(58) Field of Classification Search
CPC ............. B01D 3/36; B01D 3/42; C07C 51/46
USPC .......................................... 203/1, 15, 16, 60
See application file for complete search history.

(56) References Cited

U.S. PATENT DOCUMENTS 3,844,903 A * 10/1974 Willersinn et al. ............. 203/51
5,409,579 A * 4/1995 Gualy et al. .................... 203/16
5,980,696 A * 11/1999 Parten et al. ...................... 203/1

* cited by examiner

*Primary Examiner* — Elvis O Price
(74) *Attorney, Agent, or Firm* — William J. Simmons

(57) ABSTRACT

Disclosed is a process for the separation of water from a liquid phase medium containing an aliphatic carboxylic acid using azeotropic distillation in the presence of an entrainer. The entrainer, water, and organics are subsequently separated, wherein the entrainer is recycled back to the azeotropic distillation column and organics recycled back to the oxidation reactor.

35 Claims, 3 Drawing Sheets

DEHYDRATION OF ACETIC ACID BY AZEOTROPIC DISTILLATION IN THE PRODUCTION OF AN AROMATIC ACID

FIELD OF THE INVENTION

This invention relates to the separation of water from a liquid phase medium containing an aliphatic carboxylic acid, such as acetic acid used as a solvent for oxidation reactions, and at least one other component.

BACKGROUND OF THE INVENTION

Aromatic polycarboxylic acids, such as terephthalic acid, are important chemical intermediates used for the production of industrially significant products, including polyester polymers, which can be used for fibre production and in the manufacture of containers, bottles and other molded articles.

Current technology for the manufacture of terephthalic acid involves the liquid phase oxidation of an aromatic feedstock, such as paraxylene, using molecular oxygen in a solvent. The oxidation solvent comprises a lower (e.g. $C_2$-$C_6$) aliphatic carboxylic acid, usually acetic acid and water, in the presence of a dissolved heavy metal catalyst system usually incorporating a promoter, such as bromine. Acetic acid is particularly useful as the solvent since it is relatively resistant to oxidation and increases the activity of the catalytic pathway for the oxidation of aromatic feedstock and reaction intermediates. The reaction is carried out in one or more vessels under elevated temperature and pressure, in the range of about 150 to 250° C. and 6 to 30 barA respectively and typically produces crude terephthalic acid (CTA) in high yield, e.g. at least 95%. Under these conditions the CTA precipitates from the solvent in the oxidation reactor(s) to form a slurry of CTA solids in oxidation solvent, which is maintained in suspension by agitation. The temperature of the slurry is reduced by passing through a series of crystallisers, each at successively lower pressure, before the CTA solids are separated from the oxidation reaction solvent to give the oxidation mother liquor. The separation of the CTA solids from the oxidation mother liquor occurs at positive pressure or under vacuum.

The liquid phase oxidation of paraxylene is an exothermic reaction and the solvent such as acetic acid and water are typically removed as an overhead vapor stream from the oxidation reactor as one means of controlling the temperature of reaction. The vapor stream is condensed to recover condensables, some of which may be recycled as reflux to the oxidation reactor, while other of the condensables are passed to a separation process which, in turn, allows for recovery of the aliphatic carboxylic acid solvent, having a reduced water content.

SUMMARY OF THE INVENTION

One convenient form of separation process comprises azeotropic distillation which is preferred over fractional distillation because of its improved energy efficient operation. Whilst, the presence of an entrainer to accomplish the azeotropic distillation improves the separation of water and the aliphatic carboxylic acid solvent, other organic components can be retained in the entrainer. During the azeotropic distillation these organic components can accumulate in the top section of the distillation column and can reduce the effectiveness of the separation of water from the aliphatic carboxylic acid solvent. Simply purging the accumulated organics is inefficient and incurs additional costs, since a significant amount of entrainer is lost during purge.

Therefore, there exists a need for a method of handling the organics that accumulate in the entrainer to enable an efficient and cost-effective azeotropic distillation for the dehydration of an aliphatic carboxylic acid solvent.

In accordance with the present invention, a method has been found to manage and reduce the concentration of organics in the entrainer and to avoid a reduction in the separation of water and aliphatic carboxylic acid by azeotropic distillation.

In one aspect of the invention, a process for azeotropic distillation of a solvent for an oxidation reaction is disclosed, wherein the solvent comprises an aliphatic carboxylic acid and water, comprising:
  (a) conducting the azeotropic distillation in the presence of an entrainer to produce (i) a liquid phase component comprising said aliphatic acid having a reduced water content relative to the water content in the solvent feedstock, and (ii) a stream comprising the entrainer, organics, and water;
  (b) recovering the entrainer and organics from the stream;
  (c) recycling the recovered entrainer and a first portion of the organics as reflux to the top of the azeotropic distillation as reflux; and
  (d) purging a second portion of the organics from the recovered entrainer and organics to form an organic purge stream.

In another aspect of the invention, a process for azeotropic distillation of a solvent for an oxidation reaction is disclosed, wherein the solvent comprises an aliphatic carboxylic acid and water, comprising
  (a) conducting the azeotropic distillation in the presence of an entrainer to produce (i) a liquid phase component comprising said aliphatic acid having a reduced water content relative to the water content in the solvent feedstock and (ii) a vapor phase component comprising the entrainer, organics and water;
  (b) condensing the vapor phase component to form a liquid condensate;
  (c) separating the entrainer and organics from the liquid condensate to form a liquid organic phase;
  (d) returning a first portion of the liquid organic phase to the top of the azeotropic distillation as a reflux;
  (e) forming a purge stream from a second portion of the liquid organic phase from step (d);
  (f) contacting the purge stream from step (e) with a clean aqueous stream, to produce (i) a recovered aqueous stream comprising water and entrainer and (ii) an organic stream comprising organics and entrainer;
  (g) providing the recovered aqueous stream from step (f) comprising recovered entrainer to a recovery column to recover the entrainer; and
  (h) recycling the organics stream from step (f) to the oxidation reactor or purging it from the process.

In a further aspect of the invention, a process for azeotropic distillation of a solvent for an oxidation reaction is disclosed, wherein the solvent comprises an aliphatic carboxylic acid and water, comprising
  (a) conducting the azeotropic distillation in the presence of an entrainer to produce (i) a liquid phase component comprising said aliphatic acid having a reduced water content relative to the water content in the solvent feedstock and (ii) a vapor phase component comprising the entrainer, organics, and water;
  (b) condensing the vapor phase component and forming a liquid condensate;

(c) sending the liquid condensate to a decanter separator, wherein the entrainer and organics are separated from the liquid condensate to form a liquid organic stream;

(d) returning a first portion of the liquid organic stream to the top of the azeotropic distillation as a reflux;

(e) forming an organic purge stream from a second portion of the liquid organic stream from step (d);

(f) contacting the organic purge stream from step (e) with a clean aqueous stream in an extraction unit;

(g) recovering from step (f): (i) an organic phase comprising organics and entrainer and (ii) a recovered aqueous phase comprising water and entrainer;

(h) sending the recovered aqueous phase from step (g) comprising entrainer to a recovery column to recover the entrainer; and (i) sending the organics phase from step (g) to an oxidation reactor or purging it from the process.

DETAILED DESCRIPTION

Figure 1:
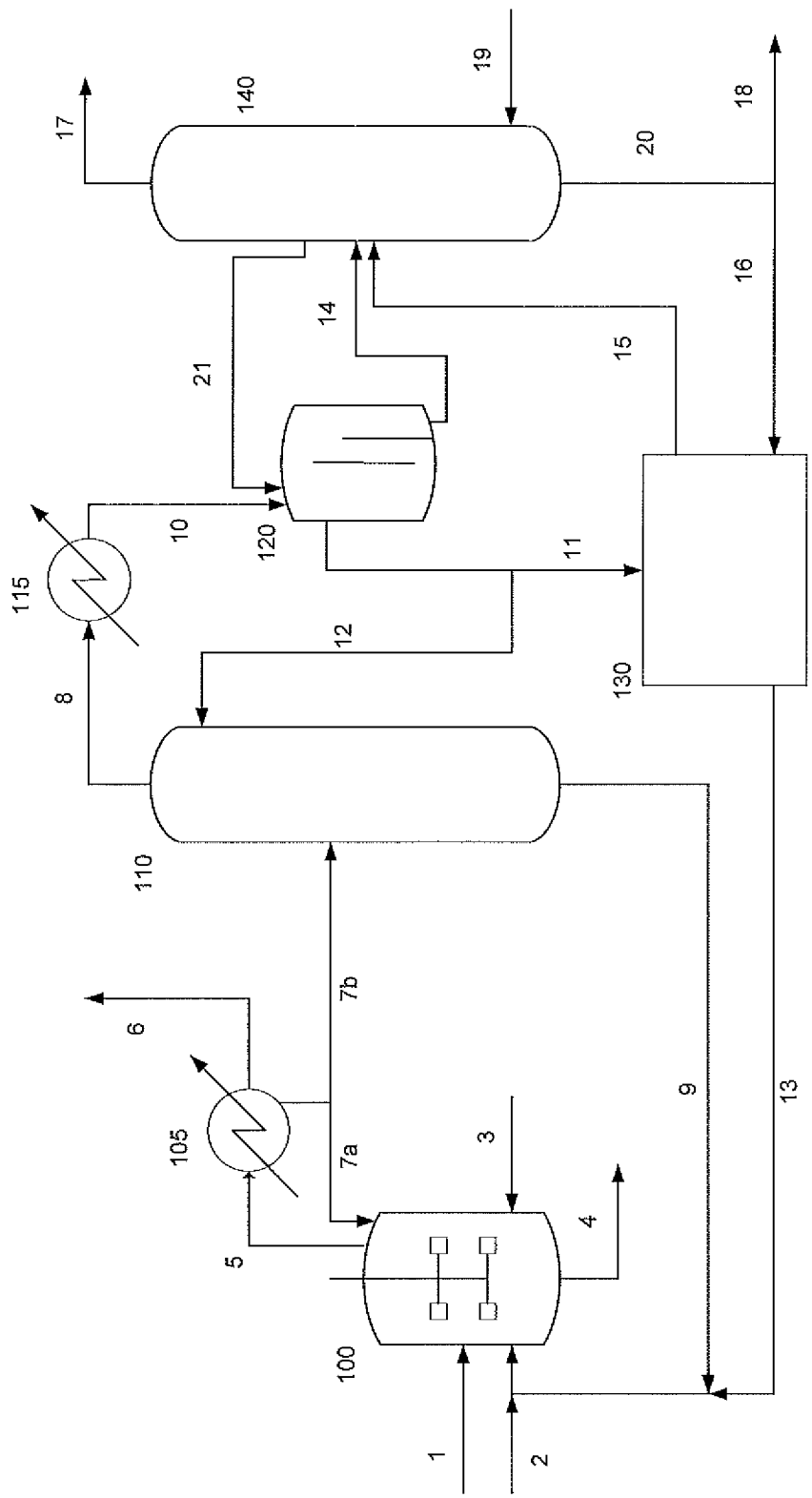
FIG. 1 is a schematic diagram of an embodiment of the invention comprising an azeotropic distillation column.

Disclosed is a process for the azeotropic distillation of a solvent for an oxidation reaction, wherein the solvent comprises an aliphatic carboxylic acid and water, comprising:

(a) conducting the azeotropic distillation in the presence of an entrainer to produce (i) a liquid phase component comprising said aliphatic acid having a reduced water content relative to the water content in the solvent feedstock, and (ii) a stream comprising the entrainer, organics, and water;

(b) recovering the entrainer and organics from the stream;

(c) recycling the recovered entrainer and a first portion of the organics as reflux to the top of the azeotropic distillation as reflux; and (d) purging a second portion of the organics from the recovered entrainer and organics to form an organic purge stream.

The separation of the organics from entrainer and water can be carried out continuously or in a batch mode.

In the disclosed processes, the entrainer can be at least one ester selected from n-butyl acetate, isobutyl acetate, n-propyl acetate, isopropyl acetate or mixtures thereof, for example isobutyl acetate, isopropyl acetate or n-propyl acetate; n-propyl acetate or isopropyl acetate; or n-propyl acetate. The entrainer can be an entrainer with a boiling point in the range of from about the boiling point of isopropyl acetate to about the boiling point of n-butyl acetate, for example from about 88° C. to about 126° C.

The organics that can accumulate in the entrainer can be minor components contained in the feedstock to the oxidation reactor that remain as inert components in the production process or react in the oxidation reactor to form byproducts that can be separated from the principle product. For a process for the production of terephthalic acid, where the feedstock to the oxidation reactor is paraxylene minor components contained in the feedstock can include benzene, alkyl benzenes, such as toluene and other xylene isomers, such as o-xylene.

Byproducts generated within the manufacturing process can include aldehydes, esters, alcohols and acids corresponding to compounds in the paraxylene feedstock fed to the oxidation reactor or degradation products from the entrainer. Typically, the byproducts comprise methyl acetate, benzoic acid and volatile reaction intermediates such as p-toluic acid. Although toluene is typically present at less than 100 ppm by weight in the paraxylene feedstock, concentrations in the range from about 250 ppm by weight to about 650 ppm by weight can be used in the manufacturing process. The bromine-promoted heavy metal catalyst used for the oxidation of paraxylene is effective for the oxidation of toluene to benzoic acid, with a first-pass conversion of toluene of between about 30% to about 70%, including between about 40% to about 60%, and about 55% by weight. This results in a total conversion of toluene of about 95% by weight, including from about 70% to about 99%, and from about 85% to about 97%. The unconverted toluene exits the oxidation reactor in the vapour stream and is condensed in the reactor overheads condenser. The organics fed to the azeotropic distillation decanter can comprise entrainer and toluene.

In the disclosed processes, the recycled entrainer or reflux to the azeotropic distillation column can comprise organics at a concentration in the range from about 1% w/w to about 60% w/w of the total composition, including from about 1% w/w to about 20%, and about 2% w/w to about 10% w/w.

The aromatic carboxylic acid production processes in which the instant invention can be most applicable are those processes employed on a commercial scale for production of terephthalic acid and isophthalic acid in which the aliphatic carboxylic acid solvent is typically acetic acid.

Figure 2:
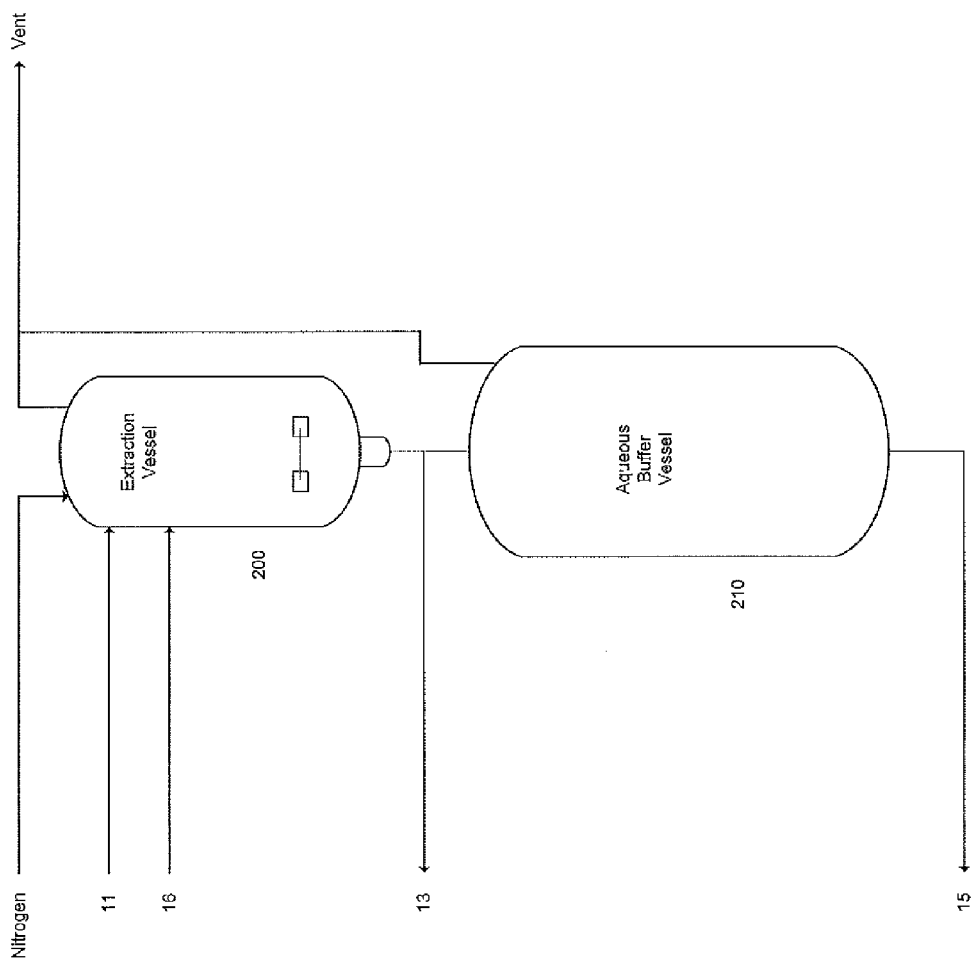
FIG. 2 is a schematic process diagram which illustrates one embodiment of the invention. The organic separation process is carried out as a batch process.
Figure 3:
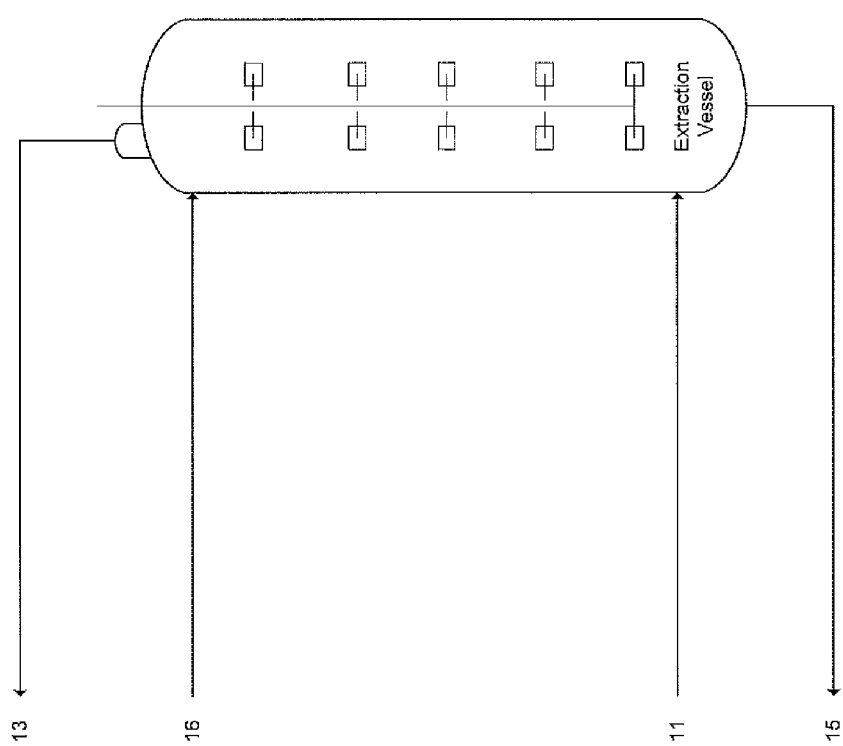
FIG. 3 is a schematic diagram of an alternative embodiment of the invention. The organic separation process is carried out as a continuous process.

FIGS. 1, 2 and 3 depict one aspect of the disclosed process, which illustrate an azeotropic distillation process and processes for the separation of organics from an entrainer used in azeotropic distillation. For simplicity a process describing aspects of the production of terephthalic acid (TA) will be referred to.

Referring to FIG. 1, an oxidation reactor 100, is fed with p-xylene as the feedstock and catalyst 1, typically a mixed-metal bromide catalyst is used comprising cobalt, manganese and HBr. Fresh acetic acid solvent 2 and molecular oxygen, typically air 3 are also fed to the oxidation reactor. The TA product as a slurry is fed to the rest of the production process 4, where additional crystallisation, separation from the acetic acid solvent and drying of the product typically occur. The oxidation of p-xylene is exothermic and acetic acid, water, solvent and other volatile components are typically removed 5 as an overhead vapor stream from the oxidation reactor as one means of controlling the temperature of reaction. The vapor stream is condensed 105 to recover condensables, some of which may be recycled as reflux to the oxidation reactor 7a, while other of the condensables are passed 7b to an azeotropic distillation column 110, a separation process for recovery of the acetic acid solvent having a reduced water content, which can be recycled 9 to the oxidation reactor 100. The non-condensables from the reactor overheads condenser pass 6 to a scrubber, before being processed further, for example to recover power using an expander.

The vapor stream from the azeotropic distillation column passes 8 to a condenser 115 and the condensate passes 10 to the azeotropic distillation decanter 120 for phase separation of the water-rich and organic-rich components in the condensate. The water-rich phase is fed 14 to the recovery column 140, where residual organics are stripped from the aqueous phase using steam heating 19 to generate essentially an entrainer-free water stream 20, an entrainer-rich recycle stream 21 and a recovery column overheads stream 17, comprising volatile components including organics and water vapour, for further processing elsewhere in the process, such as an absorber. Water 18 from the base of the recovery column 140 is used elsewhere in the production process and any excess can be purged to an effluent treatment plant.

The entrainer-rich phase from the decanter is fed as a reflux stream 12 to the azeotropic distillation column. A purge stream 11 is taken from the reflux stream 12 and fed to the organic recovery unit 130, where the water from the recovery column bottoms 16, which may be optionally cooled, is in the range from about 20° C. to about 120° C., including about 40° C. to about 100° C., and about 80° C. to about 100° C. The water is mixed with the purge stream 11, in the range from about 60° C. to about 100° C., including about 70° C. to about 90° C., to generate effective contact between the immiscible phases. Components from the purge stream comprising organics, such as toluene form the organic phase, separates by density difference from the aqueous phase comprising water and entrainer. The aqueous phase is fed 15 to the recovery column 140. The organic phase comprising toluene is fed 13 to the oxidation reactor 100, where the toluene is oxidized, in part, to benzoic acid, or the organics phase can be purged from the process. Benzoic acid is purged from the oxidation process using existing oxidation mother liquor purges and catalyst residues recovery systems. In this way, organics such as toluene are purged from the azeotropic distillation column 110.

FIG. 2 shows a batch system for the removal of organics from the azeotropic distillation reflux stream 11, which is fed into the extraction vessel 200. Aqueous condensate from the recovery column bottoms 16 (cooled or otherwise) is added to the extraction vessel and the contents agitated by a stirrer to ensure good mixing. The agitator is stopped and the vessel contents separated into two immiscible phases, wherein the lower aqueous phase flows to the aqueous buffer vessel 210. The flow is halted and additional aqueous condensate from the recovery column bottoms 16 (cooled or otherwise) can be added, before again agitating the vessel contents, allowing the organic and aqueous phases to separate before again transferring the aqueous phase to the aqueous buffer vessel 210. Addition of fresh aqueous condensate from the recovery column bottoms can be repeated as many times as required to optimize the extraction of entrainer from the azeotropic distillation reflux stream 11. The resulting aqueous phase comprising water and entrainer is fed 15 to the recovery column 140 to recover the entrainer in the recovery column side stream 21. The organics remaining are fed 13 to the oxidation reactor 100 or purged.

To accommodate the changes in liquid levels during the batch operations nitrogen can be fed to, or vented from the extraction vessel 200, typically on pressure control. The aqueous buffer vessel 210 is similarly pressure balanced. Alternatively, slight pressure variations, with minimal nitrogen feed and venting, are acceptable. This option is more efficient and cost effective, since less nitrogen control is employed.

For the batch process to operate effectively and particularly when used as part of a continuously operating production process, control of each step of the batch process must be correctly sequenced. This is best achieved using a batch sequence controller, comprising an independent programmable device, the production plant control system or other similar system, to monitor levels and flows, initiate processing steps and signal actuated valves to isolate or direct flows of the process materials.

FIG. 3 shows a continuous system for the removal of organics from the azeotropic distillation reflux stream 11. This is best done using a countercurrent extraction system, such as an agitated column and can include devices, such as those supplied by Kuhni or Scheibel. Other devices can also be used, including packed columns. The height of the column is designed to provide sufficient stages to complete the required separation of organics from the azeotropic distillation reflux purge stream 11 and prevent too high a concentration of organics in the azeotropic distillation column reflux stream 12, which would reduce the separation capacity of azeotropic distillation column 110.

Also disclosed is a process for the azeotropic distillation of a solvent for an oxidation reaction, wherein the solvent comprises an aliphatic carboxylic acid and water, comprising
  (a) conducting the azeotropic distillation in the presence of an entrainer to produce (i) a liquid phase component comprising said aliphatic acid having a reduced water content relative to the water content in the solvent feedstock and (ii) a vapor phase component comprising the entrainer, organics and water;
  (b) condensing the vapor phase component to form a liquid condensate;
  (c) separating the entrainer and organics from the liquid condensate to form a liquid organic phase;
  (d) returning a first portion of the liquid organic phase to the top of the azeotropic distillation as a reflux;
  (e) forming a purge stream from a second portion of the liquid organic phase from step (d);
  (f) contacting the purge stream from step (e) with a clean aqueous stream, to produce (i) a recovered aqueous stream comprising water and entrainer and (ii) an organic stream comprising organics and entrainer;
  (g) providing the recovered aqueous stream from step (f) comprising recovered entrainer to a recovery column to recover the entrainer; and
  (h) recycling the organics stream from step (f) to the oxidation reactor or purging it from the process.

Also disclosed is a process for the azeotropic distillation of a solvent for an oxidation reaction, wherein the solvent comprises an aliphatic carboxylic acid and water, comprising:
  (a) conducting the azeotropic distillation in the presence of an entrainer to produce (i) a liquid phase component comprising said aliphatic acid having a reduced water content relative to the water content in the solvent feedstock and (ii) a vapor phase component comprising the entrainer, organics, and water
  (b) condensing the vapor phase component and forming a liquid condensate;
  (c) sending the liquid condensate to a decanter separator, wherein the entrainer and organics are separated from the liquid condensate to form a liquid organic stream;
  (d) returning a first portion of the liquid organic stream to the top of the azeotropic distillation as a reflux;
  (e) forming an organic purge stream from a second portion of the liquid organic stream from step (d);
  (f) contacting the organic purge stream from step (e) with a clean aqueous stream in an extraction unit;
  (g) recovering from step (f): (i) an organic phase comprising organics and entrainer and (ii) a recovered aqueous phase comprising water and entrainer;
  (h) sending the recovered aqueous phase from step (g) comprising entrainer to a recovery column to recover the entrainer; and
  (i) sending the organics phase from step (g) to an oxidation reactor or purging it from the process.

Examples

The following examples further illustrate the various aspects of the disclosed process.

A combination of physical measurements and modelling gives the results in the examples.

Continuous Extraction

Using a continuous extraction process to remove toluene from the azeotropic distillation reflux purge stream is demonstrated in Examples 1 and 2. By varying the number of theoretical extraction stages more than 75% of toluene in the azeotropic distillation reflux purge stream can be removed. In this way the concentration of toluene in the azeotropic distillation reflux stream is maintained at a conveniently low level of about 10% w/w or less and the efficient separation of water from the oxidation solvent in the azeotropic distillation stage of the manufacturing process is maintained. In contrast, Comparative example 1 shows that, without suitable treatment of an azeotropic distillation reflux purge stream, the concentration of toluene cannot be controlled and once the concentration of organic impurities, comprising toluene, rises to about 20% or more the separation capacity of the azeotropic distillation stage is significantly reduced.

|  | Example 1 | Comparative Example 1 | Example 2 |
|---|---|---|---|
| Concentration of toluene in reflux stream to azeotropic distillation (and in purge stream) (% w/w) | 10 | ≥30 | 10 |
| Number of extraction stages | 3 | 0 | 4 |
| Water:organic flow ratio (w/w) | 37.3 |  | 37.2 |
| Entrainer recovered to aqueous phase (% of feed) | 98.5 | 0 | 99.0 |
| Toluene in organic purge stream (% of feed to organic recovery unit) | 75.5 | 0 | 82.1 |

Batch Extraction

A batch extraction process to remove toluene from the azeotropic distillation reflux purge stream is demonstrated in Examples 3 and 4. By varying the number of theoretical extraction stages more than 60% of toluene in the azeotropic distillation reflux purge stream can be removed. In this way the concentration of toluene in the azeotropic distillation reflux stream is maintained at a conveniently low level of about 10% w/w or less and the efficient separation of water from the oxidation solvent in the azeotropic distillation stage of the manufacturing process is maintained. In contrast, Comparative example 3 shows that, without suitable treatment of an azeotropic distillation reflux purge stream, the concentration of toluene cannot be controlled and once the concentration of organic impurities, comprising toluene, rises to about 20% or more the separation capacity of the azeotropic distillation stage is significantly reduced.

|  | Example 3 | Comparative Example 3 | Example 4 |
|---|---|---|---|
| Concentration of toluene in reflux stream to azeotropic distillation (and in purge stream) (% w/w) | 10 | ≥30 | 10 |
| Number of extraction stages | 3 | 0 | 4 |
| Water:organic flow ratio (w/w) | 45.2 |  | 45.4 |
| Entrainer recovered to aqueous phase (% of feed) | 93.8 | 0 | 94.9 |
| Toluene in organic purge stream (% of feed to organic recovery unit) | 60.8 | 0 | 61.3 |

While the invention has been described in conjunction with various aspects thereof, it is evident that many alternatives, modifications and variations will be apparent to those skilled in the art in light of the foregoing description. Accordingly, the invention is intended to embrace all such alternatives, modifications and variations as fall within the spirit and scope of the claims.

What is claimed is:

1. A process for the azeotropic distillation of a solvent for an oxidation reaction, wherein the solvent comprises an aliphatic carboxylic acid and water, the process comprising:
   (a) conducting the azeotropic distillation in the presence of an entrainer to produce (i) a liquid phase component comprising said aliphatic acid having a reduced water content relative to the water content in the solvent feedstock and (ii) a vapor phase component comprising the entrainer, organics and water;
   (b) condensing the vapor phase component to form a liquid condensate;
   (c) separating the entrainer and organics from the liquid condensate to form a liquid organic phase;
   (d) returning a first portion of the liquid organic phase to the top of the azeotropic distillation as a reflux;
   (e) forming a purge stream from a second portion of the liquid organic phase from step (d);
   (f) contacting the purge stream from step (e) with a clean aqueous stream, to produce (i) a recovered aqueous stream comprising water and entrainer and (ii) an organic stream comprising organics and entrainer;
   (g) providing the recovered aqueous stream from step (f) comprising recovered entrainer to a recovery column to recover the entrainer; and
   (h) recycling the organics stream from step (f) to the oxidation reactor or purging it from the process.

2. The process of claim 1 wherein the entrainer has a boiling point in the range from about the boiling point of isopropyl acetate to about the boiling point of n-butyl acetate.

3. The process of claim 1 wherein the entrainer has a boiling point in the range of from about 88° C. to about 126° C.

4. The process of claim 1 wherein the liquid organics phase comprises at least one organic impurity compound selected from the group consisting of benzene, paraxylene, and toluene.

5. The process of claim 4 wherein the organic impurity compound is toluene.

6. The process of claim 4 or 5 wherein the liquid organic phase returned to the top of the azeotropic distillation as a reflux contains the organic impurity compounds in a concentration in the range of from about 1% w/w to about 60% w/w of the total composition.

7. The process of claim 6 wherein the liquid organic phase returned to the top of the azeotropic distillation as a reflux contains the organic impurity compounds in a concentration in the range of from about 1% w/w to about 20% w/w of the total composition.

8. The process of claim 7 wherein the liquid organic phase returned to the top of the azeotropic distillation as a reflux contains the organic impurity compounds in a concentration in the range of from about 2% w/w to about 10% w/w of the total composition.

9. The process of claim 1 wherein the clean aqueous stream at step (f) is at a temperature in the range from about 20° C. to about 120° C.

10. The process of claim 1 wherein the recovered aqueous stream at step (g) is at a temperature in the range from about 20° C. to about 120° C.

11. The process of claim 6 wherein the entrainer in the recovered aqueous stream fed to the recovery column is greater than about 70% of the entrainer in the purge stream from the azeotropic distillation reflux stream.

12. The process of claim 6 wherein the entrainer in the recovered aqueous stream fed to the recovery column is greater than about 80% of the entrainer in the purge stream from the azeotropic distillation reflux stream.

13. The process of claim 6, wherein the organic impurity compounds fed to the oxidation reactor or purged is greater than about 40% of the organic impurity compounds in the purge stream from the azeotropic distillation reflux stream.

14. The process of claim 6 wherein the organic impurity compounds fed to the oxidation reactor or purged is greater than about 50% of the organic impurity compounds in the purge stream from the azeotropic distillation reflux stream.

15. The process of claim 6, wherein the entrainer in the recovered aqueous stream fed to the recovery column is greater than about 80% of the entrainer in the purge stream from the azeotropic distillation reflux stream and the organic impurity compounds fed to the oxidation reactor or purged is greater than about 50% of the organic impurity compounds in the purge stream from the azeotropic distillation reflux stream.

16. A process for azeotropic distillation of a solvent for an oxidation reaction, wherein the solvent comprises an aliphatic carboxylic acid and water, the process comprising:
    a. conducting the azeotropic distillation in the presence of an entrainer to produce (i) a liquid phase component comprising said aliphatic acid having a reduced water content relative to the water content in the solvent feedstock, and (ii) a stream comprising the entrainer, organics, and water;
    b. recovering the entrainer and organics from the stream;
    c. recycling the recovered entrainer and a first portion of the organics as reflux to the top of the azeotropic distillation as reflux; and
    d. purging a second portion of the organics from the recovered entrainer and organics to form an organic purge stream.

17. The process of claim 16 wherein the entrainer has a boiling point in the range from about the boiling point of isopropyl acetate to about the boiling point of n-butyl acetate.

18. The process of claim 16 wherein the entrainer has a boiling point in the range of from about 88° C. to about 126° C.

19. The process of claim 16 wherein the organics is at least one organic impurity compound selected from the group consisting of benzene, paraxylene, and toluene.

20. The process of claim 19 wherein the organic impurity compound is toluene.

21. A process for azeotropic distillation of a solvent for an oxidation reaction, wherein the solvent comprises an aliphatic carboxylic acid and water, the process comprising:
    a. conducting the azeotropic distillation in the presence of an entrainer to produce (i) a liquid phase component comprising said aliphatic acid having a reduced water content relative to the water content in the solvent feedstock and (ii) a vapor phase component comprising the entrainer, organics and water;
    b. condensing the vapor phase component to form a liquid condensate;
    c. sending the liquid condensate to a decanter separator, wherein the entrainer and organics are separated from the liquid condensate to form a liquid organic stream;
    d. returning a first portion of the liquid organic stream to the top of the azeotropic distillation as a reflux;
    e. forming a purge stream from a second portion of the liquid organic phase from step (d);
    f. contacting the organic purge stream from step (e) with a clean aqueous stream in an extraction unit;
    g. recovering from step (f): (i) an organic phase comprising organics and entrainer and (ii) a recovered aqueous phase comprising water and entrainer;
    h. sending the recovered aqueous phase from step (g) comprising entrainer to a recovery column to recover the entrainer; and
    i. sending the organics phase from step (g) to an oxidation reactor or purging it from the process.

22. The process of claim 21 wherein the entrainer has a boiling point in the range from about the boiling point of isopropyl acetate to about the boiling point of n-butyl acetate.

23. The process of claim 21 wherein the entrainer has a boiling point in the range of from about 88° C. to about 126° C.

24. The process of claim 21 wherein the organics is at least one organic impurity compound selected from the group consisting of benzene, paraxylene, and toluene.

25. The process of claim 24 wherein the organic impurity compound is toluene.

26. The process of claim 24 or 25 wherein the liquid organic phase returned to the top of the azeotropic distillation as a reflux contains the organic impurity compound in a concentration in the range of from about 1% w/w to about 60% w/w of the total composition.

27. The process of claim 26 wherein the liquid organic phase returned to the top of the azeotropic distillation as a reflux contains the organic impurity compound in a concentration in the range of from about 1% w/w to about 20% w/w of the total composition.

28. The process of claim 27 wherein the liquid organic phase returned to the top of the azeotropic distillation as a reflux contains the organic impurity compound in a concentration in the range of from about 2% w/w to about 10% w/w of the total composition.

29. The process of claim 21 wherein the clean aqueous stream at step (f) is at a temperature in the range from about 20° C. to about 120° C.

30. The process of claim 21 wherein the recovered aqueous stream at step (g) is at a temperature in the range from about 20° C. to about 120° C.

31. The process of claim 26 wherein the entrainer in the recovered aqueous stream fed to the recovery column is greater than about 70% of the entrainer in the purge stream from the azeotropic distillation reflux stream.

32. The process of claim 26 wherein the entrainer in the recovered aqueous stream fed to the recovery column is greater than about 80% of the entrainer in the purge stream from the azeotropic distillation reflux stream.

33. The process of claim 26, wherein the organic impurity compounds fed to the oxidation reactor or purged is greater than about 40% of the organic impurity compounds in the purge stream from the azeotropic distillation reflux stream.

34. The process of claim 26 wherein the organic impurity compounds fed to the oxidation reactor or purged is greater than about 50% of the organic impurity compounds in the purge stream from the azeotropic distillation reflux stream.

35. The process of claim 26, wherein the entrainer in the recovered aqueous stream fed to the recovery column is greater than about 80% of the entrainer in the purge stream from the azeotropic distillation reflux stream and the organic impurity compounds fed to the oxidation reactor or purged is greater than about 50% of the organic impurity compounds in the purge stream from the azeotropic distillation reflux stream.

* * * * *